(12) United States Patent
Batcho et al.

(10) Patent No.: US 6,331,642 B1
(45) Date of Patent: Dec. 18, 2001

(54) VITAMIN $D_3$ ANALOGS

(75) Inventors: Andrew David Batcho, North Caldwell; Bernard Michael Hennessy, Nutley; Milan Radoje Uskokovic, Upper Montclair, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/578,324

(22) Filed: May 24, 2000

Related U.S. Application Data

(60) Provisional application No. 60/143,413, filed on Jul. 12, 1999.

(51) Int. Cl.[7] .......................... C07C 401/00; A61K 31/59
(52) U.S. Cl. ................................. 552/653; 514/167
(58) Field of Search .................. 552/653; 514/167

(56) References Cited

U.S. PATENT DOCUMENTS

| | | | |
|---|---|---|---|
| 4,749,710 | 6/1988 | Truitt et al. | 514/167 |
| 5,087,619 | * 2/1992 | Baggiolini et al. | 514/167 |
| 5,401,733 | * 3/1995 | Mclane et al. | 514/167 |
| 5,428,029 | * 6/1995 | Doran et al. | 514/167 |
| 5,451,574 | * 9/1995 | Baggiolini et al. | 514/167 |
| 6,040,300 | * 3/2000 | Brasitus et al. | 514/167 |

FOREIGN PATENT DOCUMENTS 0 796 843   9/1997   (EP) .

OTHER PUBLICATIONS

Hisatake et al. (Cancer Res. 59(16), pp. 4023–4029, (Aug. 15, 1999).*
Baggiolini et al. (CA 112:36267, abstract of EP 325,279), 1989.*
Zhang et al. (CA 122:72583, abstract of Cell Proliferation (1994(, 27(11), 643–54).*
Schwartz et al. (CA 121:292155, abstract of Anticancer Res. (1994), 14(3A), 1077–81).*
Lamire et al. (CA 122:24528, abstract of Endocrinology (1994), 135(6), 2818–21).*
Jung et al. (CA 122:159343, abstract of Han'guk Yongyang Siklyong Hakhoechi (1994), 23(3), 443–52.*
Bishop et al. (CA 122:76909, abstract of J. Bone Miner. Res. (1994), 9(8), 1277–88, 1989.*

* cited by examiner

*Primary Examiner*—Sabiha Qazi
(74) *Attorney, Agent, or Firm*—George W. Johnston; Patricia S. Rocha-Tramaloni; Robert A. Silverman

(57) ABSTRACT

Compounds of the formula (I)

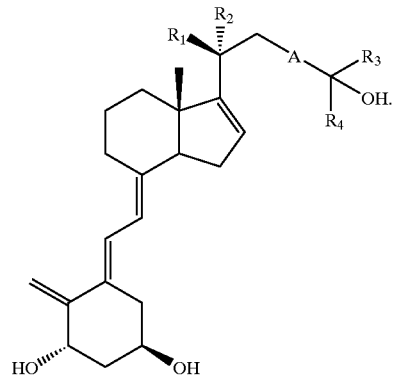

wherein $R_1$ is hydrogen or an alkyl group;
$R_2$ is hydrogen or an alkyl group; or
$R_1$, $R_2$ and $C_{20}$ together are cyclopropyl;

A is 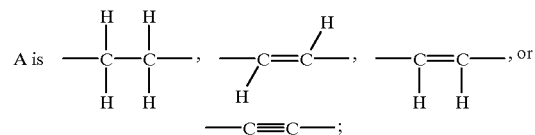

$R_3$ is alkyl, hydroxy-alkyl or fluoroalkyl; and
$R_4$ is alkyl, hydroxy-alkyl or fluoroalkyl which are useful in the treatment of breast cancer, prostate cancer, myeloid leukemia benign prostate growth, baldness and osteoporosis.

7 Claims, No Drawings

VITAMIN $D_3$ ANALOGS

This application claims priority of Provisional application No. 60/143,413, filed on Jul. 12, 1995.

SUMMARY OF THE INVENTION

The invention relates to a compound of the formula

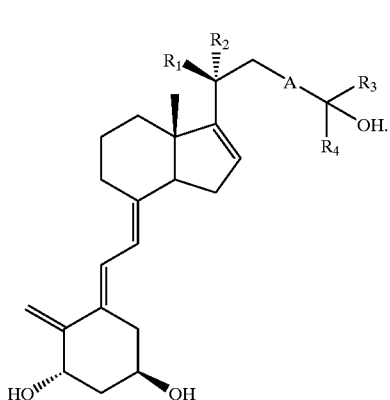

(I)

wherein
 $R_1$ is hydrogen or an alkyl group;
 $R_2$ is hydrogen or an alkyl group; or
 $R_1$, $R_2$ and $C_{20}$ together are cyclopropyl;

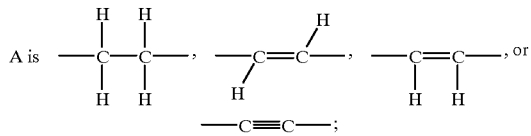

$R_3$ is alkyl, hydroxy-alkyl or fluoroalkyl; and
$R_4$ is alkyl, hydroxy-alkyl or fluoroalkyl.

It has been found that the compounds of formula I induce inhibition of proliferation in prostate, breast and myeloid leukemic cancer cell lines. Accordingly, the compounds of formula I are useful as agents for the treatment of prostate cancer, breast cancer, and for the treatment of leukemia.

It has also been found that the compounds of formula I have antiandrogenic activity. Accordingly, the compounds of formula I are useful for treating benign prostate growth, baldness and cancer of the prostate.

It has also been found that the compounds of formula I have activity making them useful for the treatment of sebaceous gland diseases such as acne or seborheic dermatitis.

It has also been found that the compounds of formula I have activity making the compounds useful for treating osteoporosis.

DETAILED DESCRIPTION OF THE INVENTION

As used herein, the term "alkyl group" denotes a straight or branched chain alkyl group having from 1–4 carbon atoms, for example, methyl, ethyl, propyl, isopropyl, butyl, t-butyl and the like. The term "hydroxy-alkyl" denotes an alkyl group having a hydroxy substituent on any of the carbon atoms of the alkyl group. The term "fluoro-alkyl" denotes an alkyl group having one, two or three fluorine atoms substituted on any of the carbon atoms of the alkyl group.

In the formulas presented herein, the various substituents are illustrated as joined to the nucleus by one of the following notations: a wedged solid line ◥ indicating a substituent which is above the plane of the molecule; and a wedged dotted line ⋯⫶⫶⫶⫶ indicating a substituent which is below the plane of the molecule.

Preferably, $R_1$ is hydrogen and $R_2$ is alkyl, or $R_1$ is alkyl and $R_2$ is hydrogen. More preferably, $R_1$ is hydrogen and $R_2$ is methyl or $R_1$ is methyl and $R_2$ is hydrogen.

Preferably, $R_3$ and $R_4$ are independently, alkyl, hydroxy-alkyl or trifluoro-alkyl. More preferably, $R_3$ and $R_4$ are, independently, methyl, hydroxy-methyl or trifluoro-methyl.

Preferably, A is

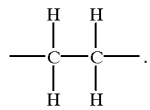

The most preferred compound of formula I is 1,25-dihydroxy-16-ene-5,6-trans-cholecalciferol.

The compounds of formula I are prepared as hereafter described, with particular reference the Formula Scheme below.

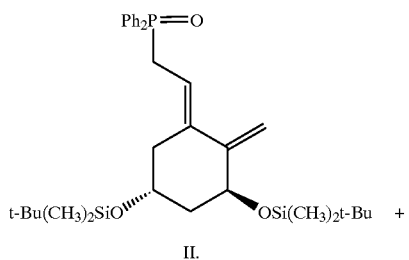

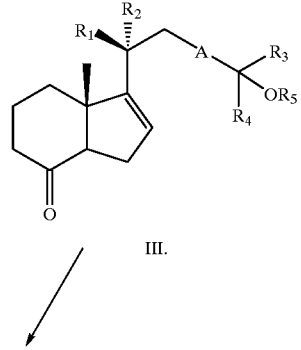

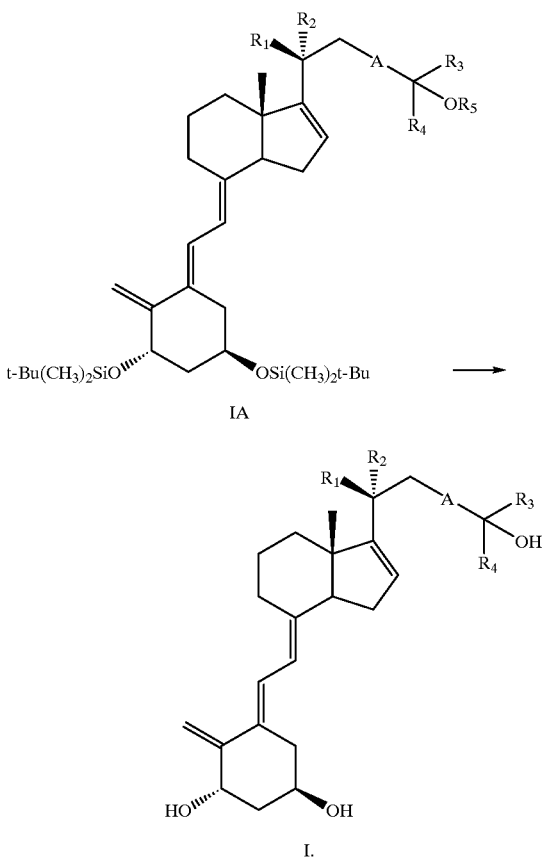

$R_5$ is hydrogen or trimethylsilyl.

In the above Formula Scheme, wherein Ph is phenyl, the compound of formula II, which is the compound [3S-(1E, 3β,5α)-2-[3,5-bis(dimethylethyl)dimethylsilyl]oxy]-2-methylene-cyclohexylidene]ethyl]diphenylphosphine oxide, is converted to a compound of formula IA by reaction with a compound of formula III.

The reaction is carried out at −60° C. to −90° C., in a polar aprotic, organic solvent, such as dry ether or more preferably dry tetrahydrofuran, in the presence of a strong base such as an alkyl lithium like butyl lithium.

The protecting groups of compounds of formula IA are removed by reaction with a flouride salt, such as tetrabutyl-ammonium fluoride in a polar, organic solvent such as ether, or more preferably tetrahydrofuran, to yield the corresponding compound of formula I.

The compound of formula II is prepared as hereinafter described in Examples 1–6, or alternatively, as described in Examples 7–8.

Compounds of formula III are known (for example, in U.S. Pat. No. 5,087,619) or can be prepared according to known methods.

The useful activity of compounds of formula I as agents for the treatment of prostate cancer, breast cancer, and for the treatment of leukemia can be demonstrated by the following test processes which are known in the art.

Materials selected for use herein and procedures employed were as follows:

Cell lines. The breast cancer cell line (MCF-7), prostate cancer cell line (LNCaP) and myeloid leukemia cell line (HL-60) were maintained as follows: MCF-7 cells were maintained in Dulbecco's Modified Eagle Media (DMEM) with 10% fetal calf serum (FCS); LNCaP and HL-60 were cultured in RPMI1640 with 10% FCS; All three cell lines were maintained in a 37° C. incubator containing 5% $CO_2$.

Vitamin $D_3$ Compounds. The vitamin $D_3$ compounds were dissolved in absolute ethanol at $10^{-3}$ M as stock solution, which were stored at −20° C. and protected from light. For in vitro use, compounds were diluted in DMEM or RPMI medium. For in vivo use, compounds were diluted with phosphate buffered saline (PBS). An aliquot was used only once and LNCaP cells were trypsinized. Washed single-cell suspensions of cells were enumerated and plated into 24-well flat-bottomed plates with a total of $1 \times 10^{-3}$ cells/well in a volume of 400 µl/well. The feeder layer was prepared with agar that had been equilibrated at 42° C. Prior to this step, compounds were pipetted into wells. After incubation, the colonies were counted. All experiments were done at least three times using triplicate plates per experimental point.

Serum Calcium Levels in vivo. Twenty-eight male Balb/c mice at 8 to 9 weeks of age were maintained in pathogen-free conditions and fed a standard laboratory diet. Four mice per group were injected intraperitoneally every other day (except Saturday and Sunday) with either vitamin $D_3$ compound or diluant (100 µl/mouse) for 3 weeks. Doses of 1,25(OH)$_2$-16-ene-5,6-trans-$D_3$ were: 0.1, 0.5, 1.0, and 2.0 µg. Doses of 1,25(OH)$_2D_3$ were 0.1 µg/mouse. Control mice were injected with 100 µl of PBS. Serum calcium values were measured every week by the quantitative, colorimetric detection assay.

Pulse-Exposure Experiments. The MCF-7 cells were incubated in liquid culture with $10^{-7}$ of 1,25(OH)$_2D_3$ or 1,25(OH)$_2$-16-ene-5,6-trans-$D_3$ for various duration. After incubation, these cells were carefully washed twice with PBS and viable cells were counted and plated into 24-well plates for soft agar colony assay, as previously described.

Cell Cycle Analysis by Flow Cytometry. Cell cycle analysis was performed on MCF-7 cells incubated for 4 days with either 1,25(OH)$_2D_3$ or 1,25(OH)$_2$-16-ene-5,6-trans-$D_3$ at $10^{-7}$ M. The cells were fixed in chilled methanol overnight before staining with 50 µg/ml propidium iodide, 1 mg/ml Rnase (100 units/ml) and 0.1% NP40. Analysis was performed immediately after staining. All experiments were done at least three times independently. All data were statistically analyzed by Student's test.

Western Blot Analysis. Cells were washed twice with PBS, suspended in Lysis buffer (50 mM Tris Ph 8.0, 150 mM NaCl, 0.1% SDS, 0.5% sodium deoxycholate, 1% NP40, 100 µg/ml phenylmethylsulfonyl fluoride, 2 µg/ml aprotinin, 1 µg/ml pepstatin and 10 µg/ml leupeptin), and placed on ice for 30 minutes. After centrifugation at 15,000 g for 20 minutes at 4° C., the supernatant was collected. Protein concentrations were quantitated. Whole lysates (15 µg) were resolved by 15% sodium dodecyl sulphate polyacrylamide gel, were transferred to an immobilon polyvinylidene difuride membrane and were probed with anti-$p_{27}^{kip1}$ rabbit polyclonal antibody and anti-Actin murine monoclonal antibody. Blots were developed.

Telomerase Activity. To detect the relative telomerase activity, telomeric repeat amplification protocol (TRAP) assays were performed. For human telomerase reverse transcriptase (hTERT), total RNAs were isolated from HL-cells which were treated with either 1,25(OH)$_2D_3$ or 1,25(OH)$_2$-16-ene-5,6-trans-$D_3$ ($10^{-9}$ $10^{-8}$, and $10^{-7}$ M) for 4 days with a monophasic solution of phenol and guanidine isothiocyanate. RT-PCR was performed with 1 µg of total RNA and random hexamer primers. cDNA was amplified using primers specific for the hTERT gene or the GAPDH gene, which was used as a control. The primers used for hTERT were: 5'-CGGAAGAGTGTCTGGAGCAA-3' (sense) (SEQ ID NO: 1), and 5'-GGATGAAGCGGAGTCTGGA-3'-(antisense) (SEQ ID NO: 2). The thermal cycles were 94° C. for 90 seconds, followed by 33 cycles of 95° C. for 20 seconds, 68° C. for 40 seconds, and 72° C. for 30 seconds. Primers for the GAPDH gene were: 5'-CCATGGAGAAGGCTGGGG-3' (sense) (SEQ ID NO: 3), and 5'-CAAAGTTGTCATGGATGACC-3' (antisense) (SEQ ID NO: 4). Conditions for GAPDH amplifications were: 94° C. for 2 minutes, 26 cycles of 94° C. for 30 seconds, 62° C. for 40 seconds, 72° C. for 60 seconds, followed by 72° C. for 4 minutes. PCR products were electrophoresed on 1% agarose gel and stained with ethidium bromide.

Effect of Vitamin $D_3$ analogs on Clonogenic Assay. LNCaP cells, MCF-7 cells and HL-60 cells were cloned in soft agar in the presence of vitamin $D_3$ analogs at $10^{-11}$ to $10^{-7}$ M. Dose-response curves were drawn and the effective dose that inhibited 50% colony formation ($ED_{50}$) was determined. $1,25(OH)_2$-16-ene-5,6-trans $D_3$ was effective in inhibition of clonal proliferation of the three cell lines in a dose-dependent manner. The $ED_{50}$ of $1,25(OH)_2$-16-ene-5,6-trans-$D_3$ was $1.4\times10^{-9}$ M for LNCaP cells, $4.3\times10^{-9}$ M for MCF-7 cells, and $3.0\times10^{-11}$M for HL-60 cells, which was about 10–100 fold more potent than $1,25(OH)_2D_3$.

Serum Calcium Levels in vivo. Because hypercalcemia is a major toxicity of vitamin $D_3$ compounds, the calcemic effects of $1,25(OH)_2D_3$ were compared with $1,25(OH)_2$-16-ene-5,6-trans-$D_3$. All mice survived at 3 weeks of study. The mice that received 0.1 μg of $1,25(OH)_2D_3$ were all hypercalcemic with serum calcium levels of approximately 12 mg/dl (normal 8.5–10.5 mg/dl). In contrast, mice that received $1,25(OH)_2$-16-ene-5,6-trans-$D_3$ (0.1–2.0 μg/mouse) had almost the same calcium level (8–10 mg/dl) as the control mice (8–9 mg/dl).

Pulse-Exposure Experiments. To investigate whether the inhibition of clonogenic proliferation by vitamin $D_3$ analogs was reversible, pulse-exposure experiments were performed. The MCF-7 cells were exposed to either $1,25(OH)_2$-16-ene-5,6-trans-$D_3$ or $1,25(OH)_2D_3$ for various durations, washed thoroughly, plated in soft agar, and colony numbers were enumerated on day 14 of culture. Approximately forty and thirty percent of the clonogenic cells were inhibited by 4 days of exposure to $1,25(OH)_2$-16-ene-5,6-trans-$D_3$ and $1,25(OH)_2D_3$, respectively.

Cell cycle Analysis. Effect of $1,25(OH)_2$-16-ene-5,6-trans-$D_3$ and $1,25(OH)_2D_3$ ($10^{-7}$, 4 days) on the cell cycle of the MCF-7 cells was determined. A significant increase ($P \leq 0.05$) in the number of cells in the $G_0$–$G_1$ phase of the cell cycle occurred with a concomitant decrease in the proportion of cells in S phase.

Western Blot Analysis. The cyclin dependent kinase inhibitors known as $p21^{waf1}$ and $p27^{kip1}$ are able to inhibit the activity of cyclin kinase and thus slow the progression for the cells through the cell cycle. The control MCF-7 cells constituitively had a moderate level of expression of $p21^{waf1}$ and $p27^{kip1}$, as determined by Western blot analysis. Exposure for one day to $1,25(OH)_2$-16-ene-5,6-trans-$D_3$ ($10^{-7}$ M) increased expression of $p21^{waf1}$ and $p27^{kip1}$ by about 3.2–3.5 fold, whereas culture with $1,25(OH)_2D_3$ ($10^{-7}$ M) increased expression of $p21^{waf1}$ and $p27^{kip1}$ about 1.6–1.8 fold. Exposure of MCF-7 cells to $1,25(OH)_2$-16-ene-5,6-trans-$D_3$ ($10^{-7}$ M) for 3 days resulted in a 2.8-fold and 3.4-fold increase in expression of $p21^{waf1}$ and $p27^{kip1}$, respectively. $1,25(OH)_2D_3$ ($10^{-7}$ M, 3 days) increased expression of $p21^{waf1}$ and $p27^{kip1}$ by 4.8 fold and 3.3 fold, respectively.

The dose-dependent effect of the vitamin $D_3$ compounds on expression of $p27^{kip1}$ HL-60 cells was examined. Both $1,25(OH)_2D_3$ and $1,25(OH)_2$-16-ene-5,6-trans-$D_3$ up-regulated expression of $p27^{kip1}$ expression, and these levels markedly increased after incubation with $1,25(OH)_2$-16-ene-5,6-trans-$D_3$ (4 days, $10^{-9}$ M). Levels of $p27^{kip1}$ increased prominently when the HL-60 cells were cultured with $10^{-8}$–$10^{-7}$ M of $1,25(OH)_2D_3$.

Telomerase Activity. The effect of $1,25(OH)_2$-16-ene-5,6-trans-$D_3$ and $1,25(OH)_2D_3$ ($10^{-9}$–$10^{-7}$ M, 4 days) on telomerase activity was evaluated using the TRAP assay. Telomerase activity markedly decreased in HL-60 cells cultured with either $1,25(OH)_2$-16-ene-5,6-trans-$D_3$ $10^{-9}$ M or $10^{-7}$ M, $1,25(OH)_2D_3$.

The effects of vitamin $D_3$ analogs on hTERT expression in HL-60 cells was evaluated using RT-PCR. Both $1,25(OH)_2$-16-ene-5,6-trans-$D_3$ and $1,25(OH)_2D_3$ inhibited the expression of hTERT mRNA in a dose-dependent manner with almost complete inhibition of expression occurring at $10^{-8}$ M of $1,25(OH)_2$-16-ene-5,6-trans-$D_3$ and at $10^{-7}$ M of $1,25(OH)_2D_3$.

The useful activity of the compounds of formula I as agents for the treatment of benign prostate growth can be demonstrated by the following test processes which are known in the art.

$1,25(OH)_2$-16-ene-5,6-trans $D_3$ was evaluated for antiandrogenic activity in castrated, testosterone stimulated male Syrian hamsters. Studies demonstrated that $1,25(OH)_2$-16-ene-5,6-trans $D_3$ substantially suppressed the androgen-induced hypertrophy of the seminal vesicles and the ventral prostate gland in these animals, whereas $1,25(OH)_2D_3$ was inactive at non-toxic doses (1 μg).

Castrated male Syrian hamsters were injected daily, s.c. with 20 μg testosterone propionate and 1 μg $1,25(OH)_2$-16-ene-5,6-trans $D_3$ for 14 consecutive days. Both compounds were administered in a vehicle of 0.2 ml sesame oil each. Necropsy was performed on day 15. The prostate and seminal vesicles were removed, blotted and weighed. Data were analyzed for statistical significance using the Student's t-test and are expressed as percent inhibition of stimulated response.

TABLE I

Inhibition of Prostate And Seminal Vesicle Growth In Castrated Testosterone Stimulated Hamsters

| | | Ventral Prostate | | Seminal Vesicles | |
|---|---|---|---|---|---|
| Grp. | Treatment | mg. | Inhib. | mg ± SEM | Inhib. |
| 1. | Vehicle | 12 ± 1 | — | 36 ± 3 | — |
| 2. | Testosterone | 43 ± 5 | — | 105 ± 6 | — |
| 3. | Testosterone + $1,25(OH)_2$-16-ene-5,6-trans $D_3$ 0.1 μg | 19 ± 2 | 77% | 71 ± 1 | 48% |

***$p < 0.001$

The useful activity of the compounds of formula I as agents for the treatment of osteoporosis can be demonstrated by the following test processes which are known in the art.

Materials and Methods

Animals and Treatment

Three month old adult female rats were used. After a week of acclimatization the animals were weight grouped and treated by oral gavage at 1 ml/kg/day with several concentrations of $1,25(OH)_2$-16-ene-5,6-trans $D_3$. On day 7 of dosing, animals were bled and serum calcium levels were determined.

Compound Preparation

Compound was dissolved in 200 proof ethanol to produce a concentration of 100 μg/ml. Sesame oil vehicle and ethanol compound solution were prepared for the highest dosage concentration, then rotary evaporated at 37° to remove ethanol. Dose volume was calculated using the dosing group average body weight. Serial dilutions of vehicle dissolved compound were done to appropriate dosage concentrations.

Serum Collection and Determination

Blood (1.5 ml) was collected from each animal by orbital puncture under ether anesthesia on Day 7 of dosing. Blood was collected into serum separator tubes, centrifuged at 2000 rpm for 15 minutes and then serum aliquoted for calcium determinations. Serum calcium was determined by colorimetric assay.

Results

Serum Calcium Levels

| Group # | Treatment | Dose μg/kg/day | Serum Calcium Mean (mg/dL) | SD |
|---|---|---|---|---|
| 1 | Vehicle | 0 | 9.65 | 0.25 |
| 6 | Compound | 0.5 | 10.64 | 0.51 |
| 7 | Compound | 1 | 10.06 | 0.47 |
| 8 | Compound | 1.5 | 9.92 | 0.39 |
| 9 | Compound | 2 | 9.77 | 0.46 |

Serum calcium levels were within the normal range for dosage groups up to 2 μg/kg/day of treatment with $1,25(OH)_2$-16-ene-5,6-trans $D_3$.

Materials and Methods

Animals and Treatment

Three month old adult female rats were subjected to bilateral ovariectomy or sham surgery. After a week of acclimatization the animals were weight grouped and treated by oral gavage at 1 mg/kg of specified concentration. Dose volume was calculated weekly using the group average body weight. Dosing started 17 days post surgery and continued for 19 days. On the $20^{th}$ day animals were euthanized by carbon dioxide inhalation and left femurs excised.

Total Femoral Bone Calcium

At necropsy the left femurs from all groups were excised and soft tissue removed. The bones were measured and cut in half at mid-diaphysis; then the distal portion was cut in half longitudinally after removal of the epiphysis. The bone marrow was flushed out and the calcium was extracted by immersion in 5% TCA. The calcium content of TCA extracts was determined by using quantitative, colorimetric determination of calcium. The data were expressed as mean total bone calcium in mg/distal half femur (DHF)±serum.

Serum Collection and Determination

Blood (1.5 ml) was collected from each animal by orbital puncture under ether anesthesia on day 7 and day 18 of dosing. Blood was collected into serum separator tubes, centrifuged at 2000 rpm for 15 min. and then serum aliquoted for calcium determinations. Serum calcium was determined by colorimetric assay.

Statistics

For a verification of the effect of ovariectomy on bone calcium, the sham and ovx vehicle groups were compared using student's t-test. The ovx groups were compared by one-way analysis of variance (ANOVA), followed by Fisher's LSD to compare each treatment group to vehicle when the overall effect was statistically significant.

Results

Effect on Femur Calcium Adjusted for Body Weight

| Treatment | Dose μg/kg | Femur CA/ 100 g BW | | SEM | p-value vs Ovx |
|---|---|---|---|---|---|
| Sham/Veh. | 0.000 | 14.44 | ± | 0.31 | 0.0001 |
| Ovx/Veh. | 0.000 | 10.58 | ± | 0.33 | — |
| $1,25(OH)_2D_3$ | 0.500 | 11.91 | ± | 0.32 | 0.0026 |
| $1,25(OH)_2$-16-ene-5,6-trans $D_3$ | 2.000 | 11.49 | ± | 0.26 | 0.0368 |

Effect on Serum Calcium Levels

| Treatment | Dose μg/kg | Serum Calcium mg/dl | | SEM | p-value vs Ovx |
|---|---|---|---|---|---|
| Sham/Veh. | 0.000 | 10.48 | ± | 0.12 | NS |
| Ovx/Veh. | 0.000 | 10.41 | ± | 0.15 | — |
| $1,25(OH)_2D_3$ | 0500 | 11.74 | ± | 0.19 | 0.0001 |
| $1,25(OH)_2$-16-ene-5,6-trans $D_3$ | 2.000 | 9.98 | ± | 0.09 | NS |

We first identified the useful activity of the compounds of formula I as agents for the treatment of sebaceous gland diseases, as demonstrated by the following test procedures which are known in the art.

Two hundred μl of $(1,25)OH_2$-16-ene-5,6-trans $D_3$ was dissolved in propylene glycol, administered daily (5 days per week) by gavage to make Golden Syrian hamsters. The animals were sacrificed at 4 weeks and the ears were processed for histological evaluation. The area of the sebaceous glands was measured on histologically prepared cross sections of the ear by image analysis.

| Dose (μg/day) | % Change from Control |
|---|---|
| 10 | −50 |
| 1 | −50 |
| 0.1 | −23 |
| 0.01 | −5 |

Also examined was the total lipid fraction from one of the ears (extraction by organic solvent followed by weighing the remaining lipid material).

| Dose (μg/day) | % Change from Control |
|---|---|
| 10 | −56 |
| 1 | −37 |
| 0.1 | −25 |
| 0.01 | −26 |

The compounds of formula I can be administered orally, for the treatment of breast cancer, prostate cancer or leukemia, to humans which need such treatment. More specifically, the compounds of formula I can be administered orally to an adult human in dosages that are in the range of about 1 to 20 μg per day for such treatment.

The compounds of formula I can be administered orally, for the treatment of benign prostate growth and baldness to humans which need such treatment. More specifically, the compounds of formula I can be administered orally to an adult human in dosages that are in the range of about 1 to 20 μg per day for such treatment.

The compounds of formula I can be administered orally for the treatment of osteoporosis, in humans at a dosage of about 1 to 20 μg per day.

The compounds of formula I can be administered topically, for the treatment of baldness to humans which need such treatment. More specifically, the compounds of formula I can be administered topically in dosages that are in the range of about 5 to about 50 μg per gram of topical formulation per day, for such treatment.

The compounds of formula I can be administered orally, for the treatment of sebaceous gland diseases in humans at a dosage of about 1 to 20 μg per day.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following Examples are provided to further describe the invention and are not intended to limit it in any way.

EXAMPLE 1

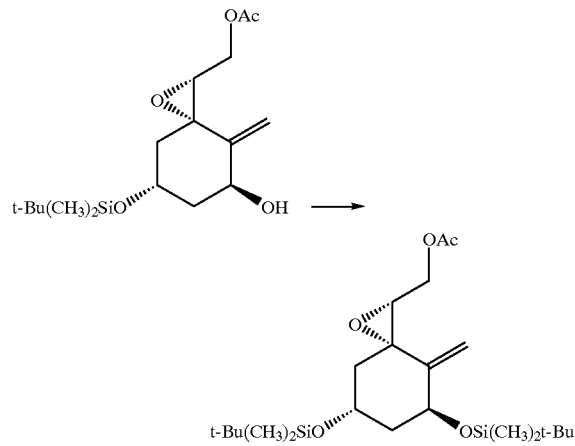

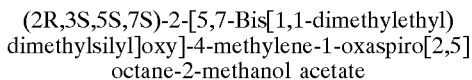

(2R,3S,5S,7S)-2-[5,7-Bis[1,1-dimethylethyl) dimethylsilyl]oxy]-4-methylene-1-oxaspiro[2,5] octane-2-methanol acetate To a magnetically stirred solution of 18.5 g (0.0523 mole) of (2R,3S,5S,7S)-5-hydroxy-4-methylene-7[(1,1-dimethylethyl)dimethylsilyloxy]-1-oxaspiro[2,5]octane-2-methanol acetate (Y. Kiegiel, P. M. Wovkulich and M. R. Uskokovic, Tetrahedron Letters, 32, pgs. 6057–6060 (1991)) and 6.8 g (0.099 mole) of imidazole in 50 ml of dimethylformamide under an argon atmosphere was added 9.8 g (0.065 mole) of t-butyldimethylsilyl chloride. The reaction mixture was stirred for 5 hours, quenched with 5 ml water, stirred for 30 min and poured in 400 ml water. It was then extracted with 2×500 ml hexane and 2×500 ml ether. The organic layers were combined, washed with 300 ml water, dried over $Na_2SO_4$ and evaporated. Chromatography on a silica-gel column gave 22.31 g (92%) of the title compound as a colorless oil.

EXAMPLE 2

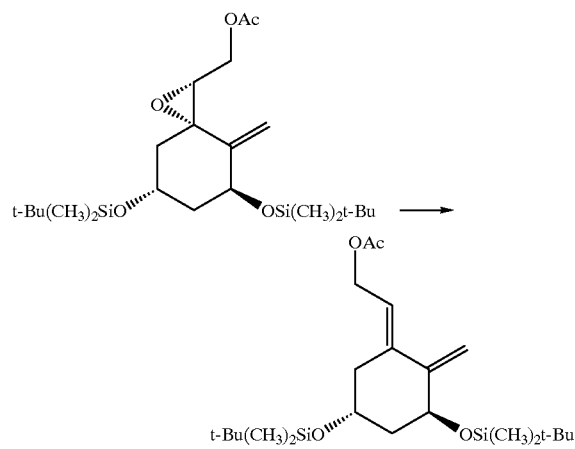

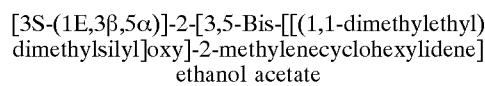

[3S-(1E,3β,5α)]-2-[3,5-Bis-[[(1,1-dimethylethyl) dimethylsilyl]oxy]-2-methylenecyclohexylidene] ethanol acetate A 3 liter 3-neck flask fitted with argon inlet, mechanical stirrer, and thermometer was charged with 500 ml of tetrahydrofuran and cooled to −60° C. in a dry ice acetone bath. Portionwise addition of 43.23 g (0.108 mole) of anhydrous tungsten hexachloride was carried out while maintaining temperature of −60° C., and then rapid dropwise addition of 200 ml of 1.6 M n-butyllithium in hexane keeping the temperature below −45° C. (ca 5 min). The dry ice-acetone bath was replaced with ice-water bath allowing temperature to reach 5° C. Color changes from blue to khaki to reddish black occurred. After 30 minutes at 5° C. a solution of 22.31 g (0.04884 mole) of (2R,3S,5S,7S)-2-[5,7-bis[[(1,1-dimethyl-ethyl)dimethylsilyl]oxy]-4-methylene-1-oxaspiro[2,5]octane-2-methanol acetate in 50 ml hexane was added rapidly dropwise over 3 minutes. After 4 hours, the reaction mixture was diluted with 2 liter of hexane, filtered through silica gel cake, which was washed with 3×500 ml of hexane-ethylacetate 9:1, and evaporated. The residue was chromatographed on a 75 g silica gel column to give 22.56 g of the crude product. Chromatography by a medium pressure silica gel column and elution with 100:1 dichloromethane-ethyl acetate mixture afforded 17.42 g (80.1%) of the title compound and small amount of the corresponding 1Z epimer.

EXAMPLE 3

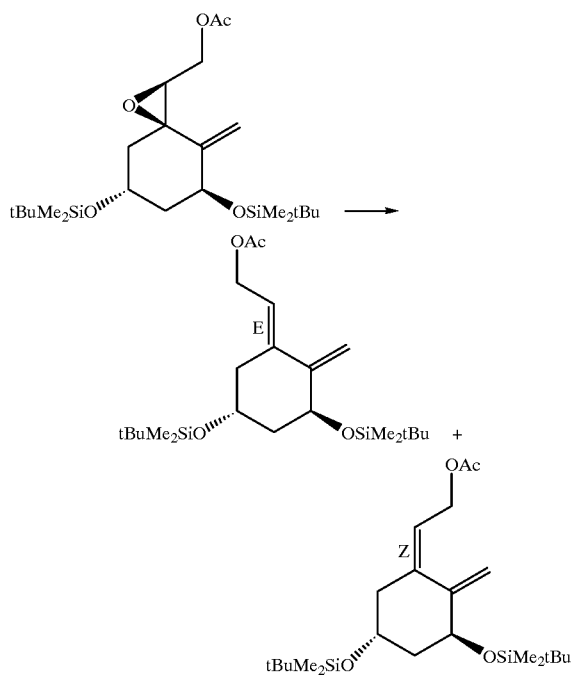

[3S-(1E,3β,5α)]-2-[3,5-Bis-[[(1,1-dimethylethyl)dimethylsilyl]oxy]-2-methylenecyclohexylidene]ethanolacetate (E-diene) and [3S-(1Z,3β,5α)]-2-[3,5-Bis-[[(1,1-dimethylethyl)dimethylsilyl]oxy]-2-methylenecyclohexylidene]ethanol acetate (Z-diene)

To 465 ml of anhydrous THF at −78 ° C. was added, with stirring, 64.3 g (160 mmol) of $WCl_6$ (blue solution), followed by the addition of 337.5 ml of 1.43 M n-BuLi in hexane (at a rate such that the internal temperature did not rise above −20 ° C.). The mixture was then allowed to warm to room temperature. A solution of 24.5 g (53.6 mmol) of (2S,3R,5S,7S)-2-[5,7-bis[[(1,1-dimethylethyl)dimethylsilyl]oxy]-4-methylene-1-oxaspiro[2,5]octane-2-methanol acetate in 65 ml of THF was added dropwise, and the mixture was stirred for 4 h. The mixture was diluted with 600 ml of pentane and filtered through a 4 cm bed of silica gel, washing with hexane/EtOAc (19:1), to give, after evaporation of the volatiles under reduced pressure, 27 g of crude diene mixture. Further purification by chromatography eluting with hexane/EtOAc (25:1) gave 21.6 g (91%) of a 2:3 Z/E dienes mixture (title compounds) which were separable by silica gel chromatography (hexane/EtOAc 40:1).

Z-diene $^1H$ NMR δ0.052 (s, 6H), 0.06 (s, 6H) 0.87 (s, 9H), 0.89 (s, 9H), 1.74–1.90 (m, 2H), 2.04 (s, 3H), 2.20 (dd, J=6.0, 12.8 Hz, 1H), 2.41 (d, J=11.1 Hz, 1H) 4.19 (m, 1H), 4.42 (m, 1H), 4.61 (dd, J=7.3, 12.1 Hz, 1H), 4.68 (dd, J=7.3, 12.1 Hz, 1H), 4.80 (s, 1H), 5.20 (s, 1H), 5.47 (t, J=7.2 Hz, 1H). $[\alpha]_D^{25}$=+1.2° (c=0.4, EtOH). Anal. Calcd. for $C_{23}H_{44}O_4Si_2$: C, 62.27; H, 10.01; Found: C, 62.55, H, 10.33.

E-diene $^1H$ NMR δ0.046 (s, 3H), 0.057 (s, 3H), 0.065 (s, 6H), 0.88 (s, 9H), 0.89 (s, 9H), 1.77 (ddd, J=3.1, 9.4, 11.9 Hz, 1H), 1.89 (m, 1H), 2.09 (s, 3H), 2.31 (dd,J=2.0, 15.2 Hz, 1H), 2.39 (dd, J=6.3, 15.2 Hz, 1H), 4.21 (br s, 1H), 4.50 (m, 1H), 4.58 (dd, J=7.2, 12.9 Hz, 1H), 4.65 (dd, J=7.2, 12.9 Hz, 1H), 4.95 (s, 1H), 4.99 (s, 1H), 5.69 (t, J=7.2 Hz, 1H). $[\alpha]_D^{25}$=+8.0° (c=0.5, EtOH). Anal. Calcd. For $C_{23}H_{44}O_4Si_2$: C, 62.67; H, 10.06; Found: C, 62.42, H, 10.01.

EXAMPLE 4

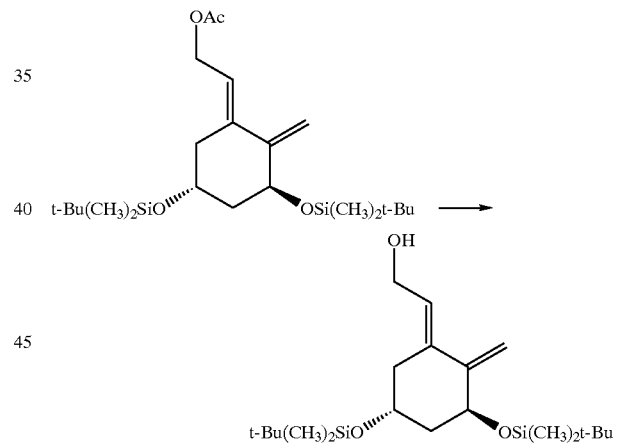

[3S-(1E,3β,5α)]-2-[3,5-Bis-[[(1,1-dimethylethyl)dimethylsilyl]oxy]-2-methylenecyclohexylidene]ethanol To a magnetically stirred solution of 10.84 g (0.0246 mole) of [3S-(1E,3β,5α)]-2-[3,5-bis-[[(1,1-dimethylethyl)dimethylsilyl]oxy]-2-methylenecyclohexylidene]ethanol acetate in 100 ml methanol under an argon atmosphere was added 3.5 g of sodium hydroxide pellets, and the reaction mixture was stirred under argon for 3 hours. It was then evaporated under reduced pressure to a 50 ml volume, diluted with 500 ml water, extracted with 2×500 ml hexane-ether 1:1. The organic layer was washed with water, dried over $Na_2SO_4$ and evaporated. It gave 9.80 g (100%) of the title compound as white solid.

EXAMPLE 5

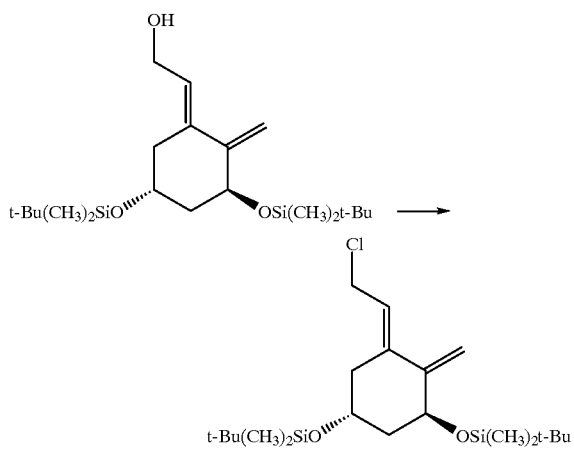

1R-(1α,3β,5E)-[[-2-Chloroethylidene)-4-methylene-1,3-cyclohexanediyl]bis(oxy)]bis(1,1-dimethylethyl) dimethylsilane To a stirred solution of 6.67 g (0.050 mole) of N-chlorosuccinimide in 150 ml dichloromethane under argon atmosphere cooled to 2° C. in an ice-acetone bath was added dropwise over 2 minutes 4 ml (0.055 mole) of dimethylsulfide. A white precipitate formed. After 30 minutes at 0° C., the bath was replaced with dry-ice acetone bath and the temperature of the reaction mixture was adjusted to −20° C. A solution of 9.8 g (0.0246 mole) of [3S-(1E,3β,5α)]-2-[3,5-bis[[(1,1-dimethylethyl)dimethylsilyl] methylene-cyclohexylidene]ethanol in 60 ml dichloromethane was added. After 15 minutes, the cooling bath was removed, and the reaction mixture was stirred for 50 minutes, and then transferred to a separatory funnel containing 500 ml water. It was extracted with 2×350 ml hexane. The organic layer was washed with 500 ml water, dried over sodium sulfate and evaporated to give 10.49 g of crude product as yellow liquid. Purification by flash chromatography gave the pure title compound as colorless oil. NMR (CDCl$_3$): δ0.03 (s, 3H), 0.05 (s, 3H), 0.07 (s, 6H), 0.87 (s, 9H), 0.89 (s, 9H), 1.70–1.94 (m, 2H), 2.34 (m, 2H), 4.13 (m, 2H), 4.28 (m, 1H), 4.53 (m, 1H), 5.00 (m, 1H), 5.03 (m, 1H), 5.78 (tm, J=8 Hz, 1H).

EXAMPLE 6

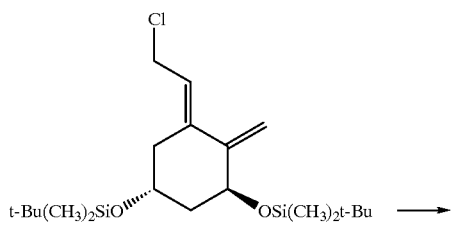

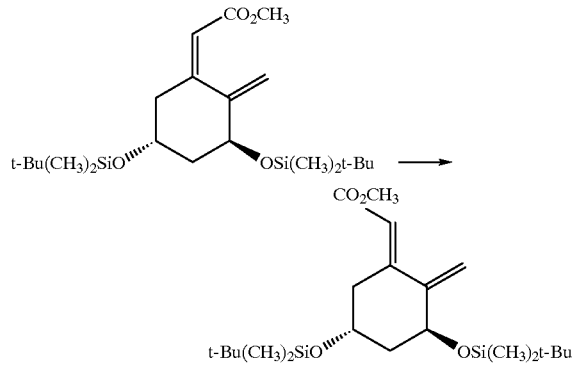

[3S-(1E,3β,5α)]-2-[3,5-Bis[[(dimethylethyl) dimethylsilyl]oxy]-2-methylenecyclohexylidene] ethyl]diphenylphosphine oxide A 1 liter 3-neck flask fitted with argon inlet, thermometer, and mechanical stirrer was charged with a solution of 10.26 g (0.0246 mole) of 1R-(1α,3β,5E)-[[-(2-chloroethylidene)-4-methylene-1,3-cyclohexanediyl]bis(oxy)]bis(1,1-dimethylethyl)dimethyl silane in 100 ml of freshly distilled anhydrous tetrahydrofuran and cooled in a dry-ice acetone bath to −65° C. Addition of 0.5 M potassium diphenylphosphide in tetrahydrofuran during 30 minutes until a red color persisted required 60 ml. After stirring for 1 hour at −65° C., 10 ml water was added and the cooling bath removed. The reaction decolorized. Then 200 ml of dichloromethane was added rapidly followed 200 ml of aqueous solution containing 10 ml of 30% hydrogen peroxide. After 1 hour, 13.5 g of sodium sulfite, 100 ml of brine and 200 ml dichloromethane were added. After shaking thoroughly, phases were separated and aqueous phase was washed with 200 ml of dichloromethane. The organic phases were washed with 200 ml of brine. The combined organic layers were dried over sodium sulfate, filtered and evaporated, to give 16.33 g of crude product. This crude product was purified by medium pressure (silica gel G-60) chromatography to give 12.54 g (87%) of the title compound as white crystals. NMR (CDCl$_3$): δ0.02 (s, 3H), 0.07 (s, 6H), 0.08 (s, 3H), 0.84 (s, 18H), 1.76 (m, 2H), 2.98–3.15 (m, 2H), 4.06 (m, 1H), 4.37 (m, 1H), 4.53 (m, 1H), 4.72 (m, 1H), 4.79 (m, 1H), 7.45 (m, 6H), 7.72 (m, 4H).

EXAMPLE 7

E-(3S,5R)-[3,5-Bis-(tert-butyl-dimethyl-silanyloxy)-2-methylenecyclohexylidene]acetic acid methyl ester (Ro 65-8821)

A solution of 4.45 g (0.01043 mole) of Z-(3S,5R)-[3,5-bis-(tert-butyl-dimethyl-silanyloxy)-2-methylene-cyclohexylidene]-acetic acid methyl ester (X) (A. Mourino, et al., Tetrahedron Letters, 38, pgs. 4713–4716 (1997)) in 100 ml hexane was irradiated with a UV-lamp for 3 hours. Evaporation gave 4.25 g (95.5%) of the title compound as colorless oil. NMR (CDCl$_3$): δ0.06 (s, 3H), 0.07 (s, 9H), 0.85 (s, 9H), 0.89 (s, 9H), 1.76 (m, 1H), 1.84 (m, 1H), 2.70 (m, 1H), 3.36 (m, 1H), 3.70 (s, 3H), 4.26 (m, 1H), 4.58 (m, 1H), 5.07 (m, 2H), 5.91 (brs, 1H).

EXAMPLE 8

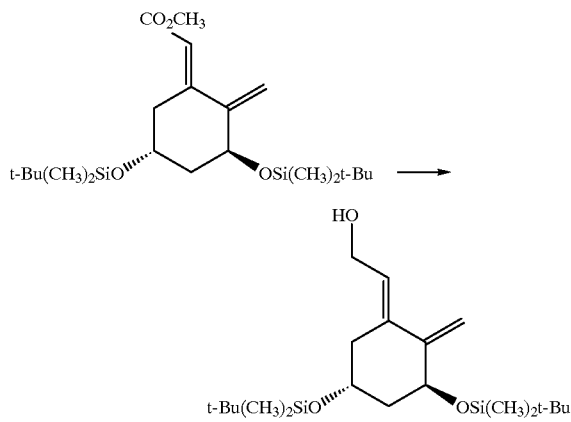

[3S-(1E,3β,5α)]-2-[3,5-Bis-[[(1,1-dimethylethyl) dimethyl-silyl]oxy]-2-methylene-cyclohexylidene] ethanol To a solution of 4.25 g (0.00996 mole) of E-(3S,5R)-[3, 5-bis-(tert-butyl-dimethyl-silanyloxy)-2-methylenecyclohexylidene]-acetic acid methyl ester in 100 ml toluene at –78° C. was added dropwise 25 ml of a 1.2 M diisobutylaluminum hydride (0.03 mole) and the reaction mixture was stirred for one hour. After addition of 5 ml methanol, the reaction mixture was allowed to warm up to room temperature. It was then diluted with 150 ml of 2M aqueous potassium-sodium tartrate and stirred vigorously. The organic phase was separated, dried over sodium sulfate and evaporated to dryness. The crude product was purified by Flash-chromatography with hexane-ethyl acetate 8:2 to yield 2.8 g (70%) of the title compound as colorless waxy solid. NMR (CDCl$_3$): δ0.05 (s, 3H), 0.07 (s, 9H), 0.88 (s, 9H), 0.91 (s, 9H), 1.74 (m, 1H), 2.06 (m, 1H), 2.26 (dm, J=13.6 Hz, 1H), 2.40 (dd, J=13.6, 5.2, 1H), 4.30–4.11 (m, 3H), 4.53 (m, 1H), 4.98 (m, 1H), 5.00 (m, 1H), 5.80 (tm, J=7 Hz, 1H).

EXAMPLE 9

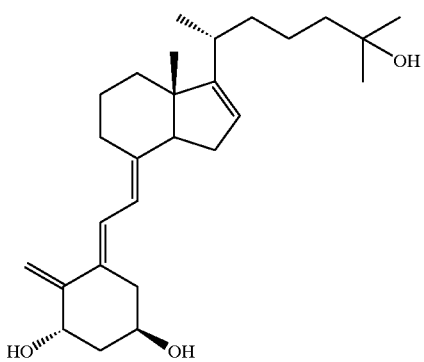

1,25-Dihydroxy-16-ene-5,6-trans-cholecalciferol

A stirred solution of 796 mg (0.00137 mole)[3S-(1E,3β, 5α)]-2-[3,5-bis[[(1,1-dimethylethyl)dimethyl-silyl]oxy]-2-methylenecyclohexylidene]ethyl]diphenylphosphine oxide in 10 ml of anhydrous tetrahydrofuran at –78° C. was treated with 0.83 ml (0.00133 mole) of a 1.6M n-butyl lithium in hexane, dropwise under argon. To thus obtained red colored solution was added a solution of 280 mg (0.000803 mole) of [3aR-[1(R*),3aα,7aβ]])-1-[1,5-dimethyl-5-[(trimethylsilyl) oxy]hexyl]-3,3a,5,6,7,7a-hexahydro-7a-methyl-4H-inden-4-one in 5 ml of tetrahydrofuran, dropwise over a 10 minute period under argon. The reaction mixture was stirred at –78° C. for 90 minutes, then quenched by addition of 40 ml of a 1:1 of 2N Rochelle salt and 2N KHCO$_3$, and allowed to warm up to room temperature. It was extracted with 3×100 ml ethyl acetate. The organic layers were washed 3× water/brine, dried over sodium sulfate and evaporated to dryness. This crude product was purified by flash chromatography on a 40 mm×6" column of silica gel with hexane-ethyl acetate 40:1, to give 278 mg of trisilylated title compound and 140 mg of starting ketone.

A solution of 278 mg (0.000389 mole) of this trisilylated intermediate in 8 ml of anhydrous tetrahydrofuran was treated with 1.9 (1.9 mmole) of a 1M tetrabutylammonium fluoride in tetrahydrofuran under argon for 17 hours. It was quenched with 6 ml water and stirred for 30 minutes. After evaporation of tetrahydrofuran in vacuo, the residual solution was extracted with 3×100 ml ethyl acetate. The organic layers were washed 4× water/brine, dried over sodium sulfate and evaporated to dryness. The crude product, 192 mg, was purified by flash chromatography on a silica gel column, which was prewashed with a 1% triethylamine:ethyl acetate solution (300 ml); elution was performed with ethyl acetate. This gave 152 mg of crystalline title compound. Sample recrystallized from tetrahydrofuran: methylformate (0.3:7) had a mp 95–100° C. $[α]_D^{25}$+160.5° (EtOH, c=0.20). λmax 272/3 nm (ε 20600).

EXAMPLE 10

Soft Gelatin Capsule Formulation I

| Item | Ingredients | mg/Capsule |
| --- | --- | --- |
| 1 | 1,25(OH)$_2$-16-ene-5,6-trans D$_3$ | 0.001–0.02 |
| 2 | Butylated Hydroxytoluene (BHT) | 0.016 |

-continued

| Item | Ingredients | mg/Capsule |
|------|-------------|------------|
| 3 | Butylated Hydroxyanisole (BHA) | 0.016 |
| 4 | Miglyol 812 qs. | 160.0 |

Manufacturing Procedure

1. Suspend BHT and BHA in Miglyol 812. Warm to about 50° C., and stir until dissolved.
2. Dissolve 1,25(OH)$_2$-16-ene-5,6-trans D$_3$ in the solution from step 1 at 50° C.
3. Cool the solution from Step 2 at room temperature.
4. Fill the solution from Step 3 in soft gelatin capsules.

Note: Perform all manufacturing steps under a nitrogen atmosphere and protect from light.

EXAMPLE 11
Soft Gelatin Capsule Formulation II

| Item | Ingredients | mg/Capsule |
|------|-------------|------------|
| 1 | 1,25(OH)$_2$-16-ene-5,6-trans D$_3$ | 0.001–0.02 |
| 2 | di-α-Tocopherol | 0.016 |
| 3 | Miglyol 812 qs. | 160.0 |

Manufacturing Procedure

1. Suspend di-α-Tocopherol in Miglyol 812. Warm to about 50° C., and stir until dissolved.
2. Dissolve 1,25(OH)$_2$-16-ene-5,6-trans D$_3$ in the solution from step 1 at 50° C.
3. Cool the solution from Step 2 at room temperature.
4. Fill the solution from Step 3 in soft gelatin capsules.

Note: Perform all manufacturing steps under a nitrogen atmosphere and protect from light.

What is claimed is:

1. A compound of the formula

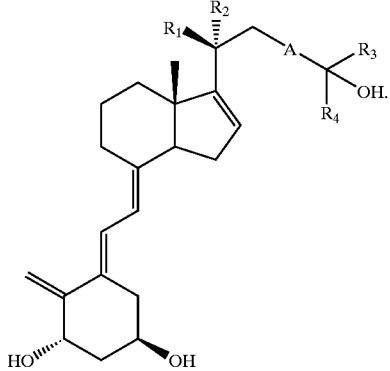

(I)

wherein $R_1$ is hydrogen or an alkyl group;

$R_2$ is hydrogen or an alkyl group; or $R_1$, $R_2$ and $C_{20}$ together are cyclopropyl;

A is —C≡C—,

,

, or

—CH$_2$—CH$_2$—;

$R_3$ is alkyl, hydroxy-alkyl or fluoroalkyl; and $R_4$ is a alkyl, hydroxyalkyl or fluoroalkyl.

2. A compound in accordance with claim 1 wherein $R_1$ is hydrogen and $R_2$ is alkyl or $R_1$ is alkyl and $R_2$ is hydrogen.

3. A compound in accordance with claim 2 wherein $R_1$ is hydrogen and $R_2$ is methyl or $R_1$ is methyl and $R_2$ is hydrogen.

4. A compound in accordance with claim 3 wherein $R_3$ and $R_4$ are, independently, alkyl, hydroxy alkyl or trifluoro-alkyl.

5. A compound in accordance with claim 4 wherein $R_3$ and $R_4$ are, independently, methyl, hydroxy-methyl or trifluoro-methyl.

6. A compound in accordance with claim 5 wherein A is

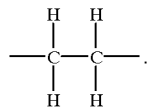

.

7. A compound in accordance with claim 6, 1,25-dihydroxy-16-ene-5,6-trans cholecalciferol.

* * * * *

```
SEQUENCE LISTING

<160> NUMBER OF SEQ ID NOS:  4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Primer for
      hTERT (sense)

<400> SEQUENCE: 1
cggaagagtg tctggagcaa                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:primer for
      hTERT (antisense)

<400> SEQUENCE: 2
ggatgaagcg gagtctgga                                               19

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:primer for
      GAPDH (sense)

<400> SEQUENCE: 3
ccatggagaa ggctgggg                                                18

<210> SEQ ID NO 4
<211> LENGTH: 20
<212> TYPE: DNA
<213> ORGANISM: Artificial Sequence
<220> FEATURE:
```

```
<223> OTHER INFORMATION: Description of Artificial Sequence:primer for
      GAPDH (antisense)

<400> SEQUENCE: 4
caaagttgtc atggatgacc                                              20
```